United States Patent
Luo

(10) Patent No.: US 11,225,499 B2
(45) Date of Patent: Jan. 18, 2022

(54) CHIRAL PLATINUM COMPLEX, METHOD FOR PREPARING THE SAME, AND METHOD FOR USING THE SAME

(71) Applicant: Hefei University of Technology, AnHui (CN)

(72) Inventor: Mei Luo, AnHui (CN)

(73) Assignee: HEFEI UNIVERSITY OF TECHNOLOGY, Hefei (CN)

( * ) Notice: Subject to any disclaimer, the term of this patent is extended or adjusted under 35 U.S.C. 154(b) by 0 days.

(21) Appl. No.: 17/022,872

(22) Filed: Sep. 16, 2020

(65) Prior Publication Data

US 2021/0115079 A1   Apr. 22, 2021

(30) Foreign Application Priority Data

Oct. 22, 2019   (CN) .......................... 201911005978.6

(51) Int. Cl.
*C07F 15/00*   (2006.01)
*A61P 35/00*   (2006.01)
*C07C 253/00*   (2006.01)

(52) U.S. Cl.
CPC .......... *C07F 15/0093* (2013.01); *A61P 35/00* (2018.01); *C07C 253/00* (2013.01); *C07C 2531/12* (2013.01)

(58) Field of Classification Search
None
See application file for complete search history.

(56) References Cited

FOREIGN PATENT DOCUMENTS

CN            106800576      *   6/2017    ..............  C07F 15/00

OTHER PUBLICATIONS

Cosaert et al. British Journal of Cancer (2002) 87, 825-833.*
CN 106800576 translation, downloaded from Google Patents Jul. 17, 2021.*

* cited by examiner

*Primary Examiner* — Clinton A Brooks
(74) *Attorney, Agent, or Firm* — Muncy, Geissler, Olds & Lowe, P.C.

(57) ABSTRACT

A chiral platinum complex having a chemical formula (I):

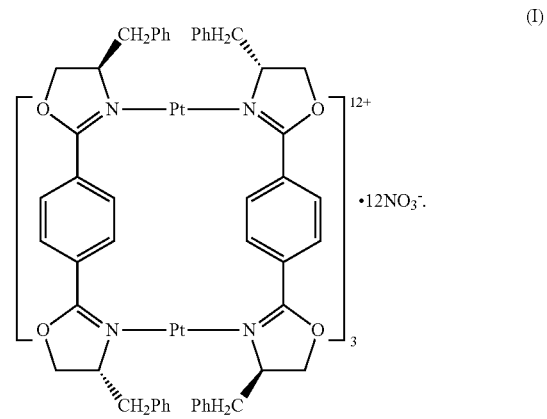

A method for synthesizing the chiral platinum complex (I), includes: dissolving 0.700 g of $Pt(DMSO)_2(NO_3)_2$ in 30 mL of dichloromethane as a solvent to yield a solution; adding 0.450 g of 1,4-(4R)-diphenyl-2-oxazolinyl benzene to the solution, and reflux a resulting mixture for reaction for 48 hrs, and stopping the reaction; filtrating reaction products; and adding dichloromethane and petroleum ether, and naturally volatilizing to yield a binuclear platinum complex single crystal. A method for condensation of benzophenone imine and trimethylsilitrile by using the chiral platinum complex as a catalyst. A method for treating cancer includes administering the chiral platinum complex to a patient in need thereof. The cancer includes: lung cancer (A549), nasopharyngeal carcinoma (KB), anti-drug-resistant nasopharyngeal carcinoma (KB-VIn), and human breast cancer (MCF-7).

1 Claim, 3 Drawing Sheets

CHIRAL PLATINUM COMPLEX, METHOD FOR PREPARING THE SAME, AND METHOD FOR USING THE SAME

CROSS-REFERENCE TO RELATED APPLICATIONS

This application claims the benefit of Chinese Patent Application No. 201911005978.6 filed Oct. 22, 2019, the contents of which are incorporated herein by reference.

BACKGROUND OF THE INVENTION

Field of the Invention

The present application relates to a metal organic coordination compound (complex) and its preparation method, particularly to a platinum-containing metal organic complex and its preparation method, and more particularly to a crystal of a platinum oxazoline complex and its synthetic method.

Description of the Related Art

Metal platinum complex has attracted wide attention due to its potential application value in anti-cancer, molecular magnet, fluorescent material and so on. There have been a lot of literature reports on the synthetic method of metal-platinum complex during recent years.

1. Cis/trans influences in platinum (II) complexes. X-ray crystal structures of cis-dichloro (dimethyl sulfide) (dimethyl sulfoxide) platinum (II) and cis-dichloro (dimethyl sulfide) (dimethyl phenyl phosphine) platinum (II), Journal of Molecular Structure, 470, 1-2, 39-47.

2. Design of chiral macrocyclic complexes based on trans-chelation of n:n metal-bidentate P, N- or N, N-ligands, Chemistry Letters (2006), 35, (2), 172-173.

SUMMARY

It is an objective of the present application to provide a Pt—N metal organic complex for application in the catalytic field, in order to solve the technical problem of selection as ligands and synthesis of a zinc complex.

To achieve the above objective, in accordance with one embodiment of the present application, there is provided a platinum complex. The platinum complex is a complex having a chemical formula (I) and prepared from dimethyl sulfoxide platinum nitrate and 1,4-(4R)-diphenyl-2-oxazolinyl benzene:

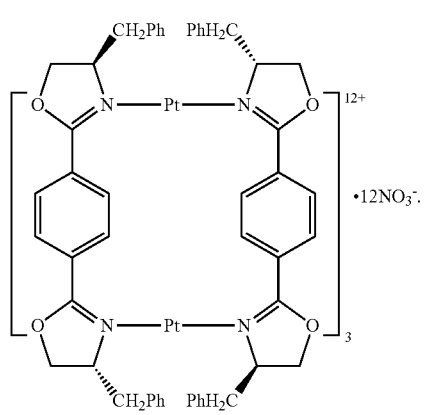

Chemical name: [1,4-(4R)-diphenyl-2-oxazolinyl benzene] platinum nitrate complex, referred to as complex (I).

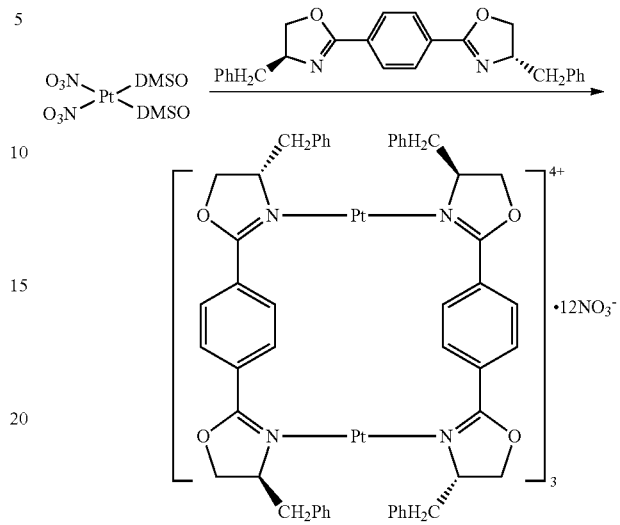

In accordance with another embodiment of the present application, there is provided a method for synthesizing the above-described chiral complex (I), comprising: reaction, separation, and purification. The method specifically comprises: dissolving 0.700 g of $Pt(DMSO)_2(NO_3)_2$ in 30 mL of dichloromethane and 20 mL of chlorobenzene as a solvent to yield a solution; adding 0.450 g of 1,4-(4R)-diphenyl-2-oxazolinyl benzene to the solution, and reflux a resulting mixture for reaction for 48 hrs, and stopping the reaction; filtrating reaction products; and adding dichloromethane and petroleum ether, and naturally volatilizing to yield a binuclear platinum complex single crystal.

In accordance with still another embodiment of the present application, there is provided a method for condensation of benzophenone imine and trimethylsilitrile by using the above-described chiral platinum complex as a catalyst. The complex shows excellent catalytic performance in the reaction of benzophenone imine and trimethylsilitrile, and its conversion rate is up to 99%.

In accordance with still another embodiment of the present application, there is provided a method for treating cancer comprising administering the chiral platinum complex of claim 1 to a patient in need thereof, wherein the cancer comprises: lung cancer (A549), nasopharyngeal carcinoma (KB), anti-drug-resistant nasopharyngeal carcinoma (KB-VIn), and human breast cancer (MCF-7).

The method for synthesizing the above-described chiral complex according to an embodiment of the present application can achieve one-step reaction to yield the target product. The process is simple and easy to operate.

DETAILED DESCRIPTION OF THE EMBODIMENTS

Figure 1:
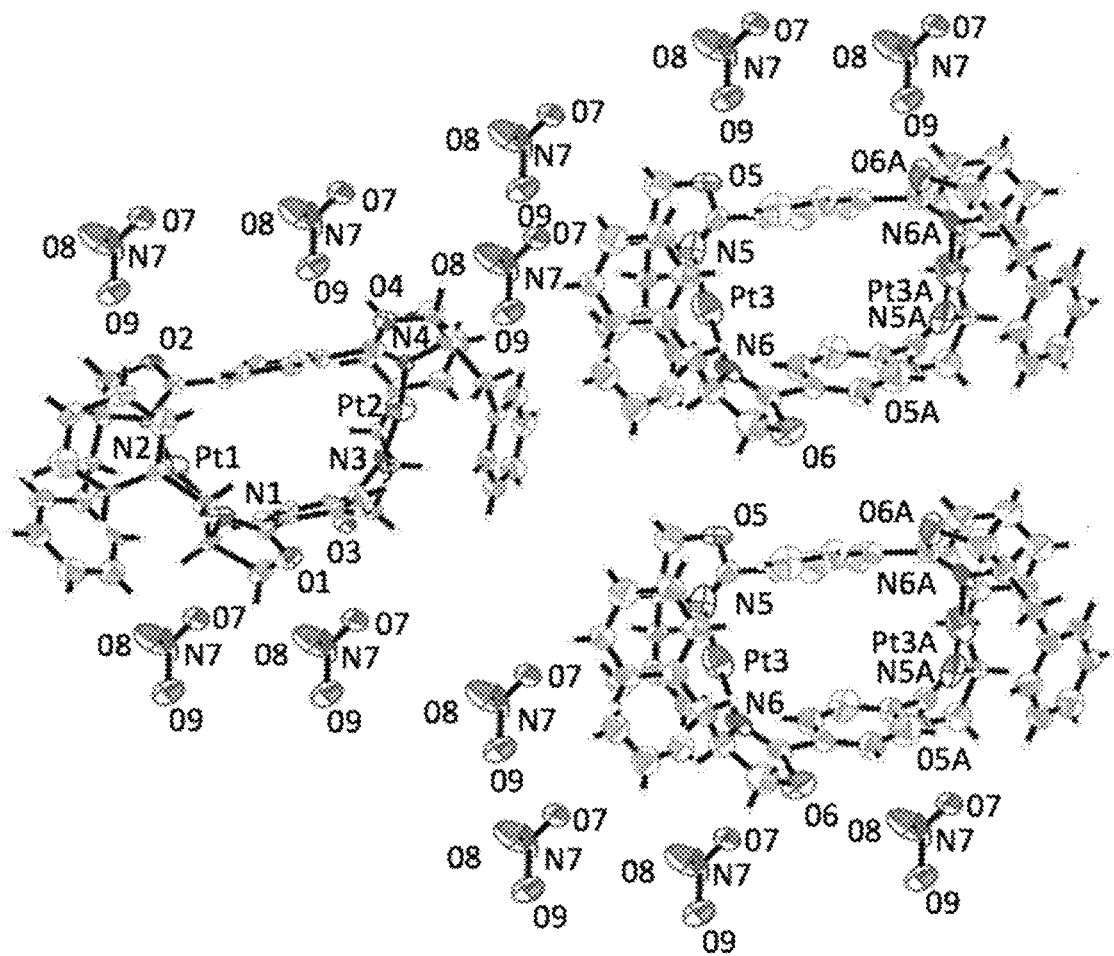
FIG. 1 is an X-ray diffraction analysis drawing of binuclear platinum complex crystal.
Figure 2:
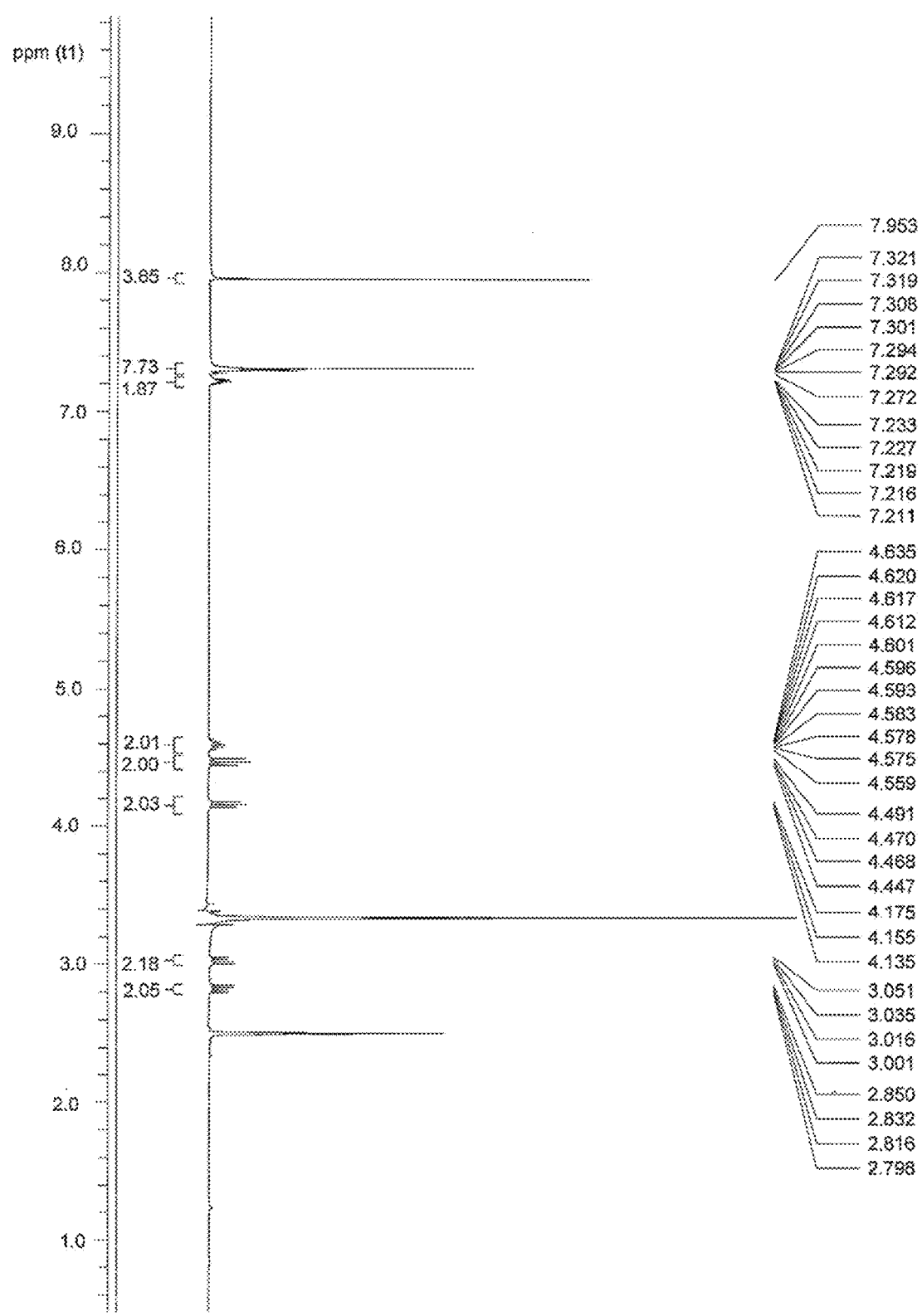
FIG. 2 is a NMR spectrogram of binuclear platinum complex crystal.
Figure 3:
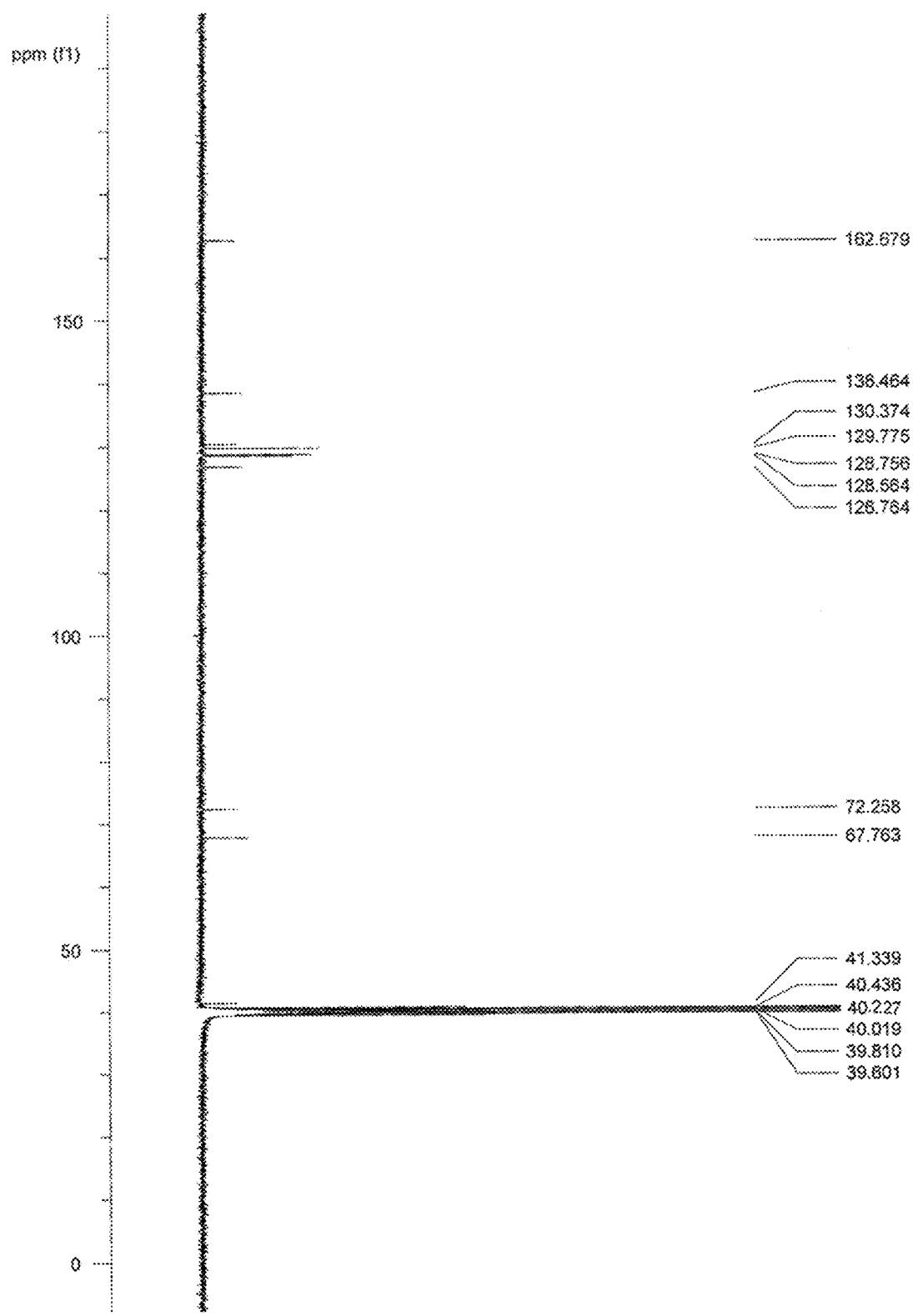
FIG. 3 is a nuclear magnetic carbon spectrum of binuclear platinum complex crystal.

1. Platinum Bichloride and Dimethyl Sulfoxide Complex 1.2042 g of platinum bichloride, 10 mL of DMSO, and 30 mL of dichloromethane were added to a 100 mL two-mouth flask to yield a mixture. The mixture was refluxed for 60 hrs, the reaction was stopped, and a resulting reaction mixture was stood. A solid dimethyl sulfoxide platinum complex was obtained with a yield thereof being 45%.

Elemental analysis results were as follows:
Test values: C: 11.78%, H: 2.91%;
Calculated values: C: 11.38%, H: 2.86%, IR (KBr): 1157, 1134, 450, 430.

2. Dimethyl Sulfoxide and Platinum Nitrate Complex

To a two-mouth flask, 0.3521 g of dimethyl sulfoxide platinum chloride, 0.5135 g of silver nitrate, and 20 mL of dichloromethane as solvent, were added for carrying out reaction in dark by using an aluminum foil at room temperature for 30 hrs. A resulting reaction mixture was filtrated and added with dichloromethane/trichloromethane in a volume ratio of 1/1 to prepare a solution. The resulting solution was naturally volatilized to obtain a dimethyl sulfoxide platinum nitrate complex in a solid form, with a yield thereof being 42%.

3. Preparation of Dimethyl Sulfoxide Binuclear Platinum Complex Crystal 0.700 g of $Pt(DMSO)_2(NO_3)_2$ were taken and dissolved with 30 mL of dichloromethane as the solvent to yield a resulting solution. 0.450 g of 1,4-(4R)-diphenyl-2-oxazolinyl benzene was added to the resulting solution for reflux reaction for 48 hrs. The reaction was stopped. Thereafter, reaction products were filtrated, and added with dichloromethane and petroleum ether, and naturally volatilized, to obtain a new single crystal of binuclear platinum complex, with a yield thereof being 90%, m.p. 121-122° C.; $[\alpha]5D=+125.0°$ (c 0.04, DMF). Elemental analysis: $C_{156}H_{144}N_{24}O_{48}Pt_6$: Test values: C, 43.90, H, 3.71, N, 7.51; Calculated values: (%) C, 43.64, H, 3.38, N, 7.83; $^1H$ NMR (600 MHz, DMSO), δ ppm 7.95 (s, 8H, ArH), 7.12-7.32 (m, 20H, ArH), 4.56-4.64 (m, 4H, CH), 4.45-4.49 (m, 4H, CH), 4.16 (t, J=7.9 Hz, 4H, CH), 3.04 and 3.02 (dd, J=6.1, 6.8 Hz, 4H, 2×CH2), 2.85 and 2.82 (dd, J=7.3, 7.3 Hz, 4H, 2×CH2); 13C NMR (150 MHz, DMSO) 162.7, 138.5, 130.4, 129.8, 128.8, 128.6, 126.8, 72.3, 67.8, 41.3; $v_{max}$ ($cm^{-1}$) 3448, 3026, 2924, 2854, 2426, 1645, 1610, 1571, 1510, 1497, 1454, 1384, 1281, 1259, 1084, 1063, 1015, 967, 919, 861, 839, 756, 728, 699;

The data of the complex crystal are as follows:
Empirical formula: $C_{156}H_{144}N_{24}O_{48}Pt_6$
Molecular weight: 4293.49
Temperature: 293.19(10)K
Wavelength: 1.54184 Å
Crystal system, spatial group: Monoclinic system, C2
crystal cell parameters: a=33.373 Å; α=90°.
b=9.580(3) Å; β=118.303(6°).
c=32.316 (9) Å; γ=90°.
Volume: 9096 (4) Å$^3$
Electric density: 2, 1.380 Mg/m$^3$
Absorption, correction parameter: 4.696 mm$^{-1}$
Number of electrons in a single cell: 3682.0.0
Crystal size: 0.20×0.12×0.06 mm
Theta angle range: 4.472 to 50
Index collection range of HKL: −39<=h<=39, −11<k<11, −38<l<=38
Collect/Independent diffraction data: 16001/4652[R(int)= 0.0752]
Method of absorption correction: Multilayer scanning
Method used for refinement: Least square method of matrix of F$^2$
Number of data/number of use limit/number of parameters: 4652/499/803
Method used for refinement: 0.995
Coincidence factor for diffraction point: R1=0.0902, ωR2=0.2485
Coincidence factor of observable diffraction: R1=0.1416, ωR2=0.2892
Maximum peak and valley on the difference Fourier diagram: 1.00 and −2892 e·Å$^{-3}$ Typical Bond Length Data for Crystal are Listed as Follows:

| Atom | Atom | Length/Å |
|---|---|---|
| $C_1$ | $C_4$ | 1.42(3) |
| $C_1$ | $N_1$ | 1.36(3) |
| $C_1$ | $O_1$ | 1.30(2) |
| $C_2$ | $C_3$ | 1.58(3) |
| $C_2$ | $O_1$ | 1.37(3) |
| $C_3$ | $C_{20}$ | 1.56(3) |
| $C_3$ | $N_1$ | 1.53(2) |
| $C_4$ | $C_5$ | 1.42(3) |
| $C_4$ | $C_9$ | 1.34(3) |
| $C_5$ | $C_6$ | 1.29(3) |
| $C_6$ | $C_7$ | 1.51(3) |
| $C_7$ | $C_8$ | 1.20(3) |
| $C_7$ | $C_{10}$ | 1.49(3) |
| $C_8$ | $C_9$ | 1.51(3) |
| $C_{10}$ | $N_3$ | 1.29(3) |
| $C_{10}$ | $O_3$ | 1.33(2) |
| $C_{11}$ | $C_{12}$ | 1.61(2) |
| $C_{11}$ | $O_3$ | 1.55(2) |
| $C_{12}$ | $C_{13}$ | 1.39(3) |
| $C_{12}$ | $N_3$ | 1.48(2) |
| $C_{13}$ | $C_{14}$ | 1.47(2) |
| $C_{14}$ | $C_{15}$ | 1.3900 |
| $C_{14}$ | $C_{19}$ | 1.3900 |
| $C_{15}$ | $C_{16}$ | 1.3900 |
| $C_{16}$ | $C_{17}$ | 1.3900 |
| $C_{17}$ | $C_{18}$ | 1.3900 |
| $C_{18}$ | $C_{19}$ | 1.3900 |
| $C_{20}$ | $C_{21}$ | 1.53(2) |
| $C_{21}$ | $C_{22}$ | 1.3900 |
| $C_{21}$ | $C_{26}$ | 1.3900 |
| $C_{22}$ | $C_{23}$ | 1.3900 |
| $C_{23}$ | $C_{24}$ | 1.3900 |
| $C_{24}$ | $C_{25}$ | 1.3900 |
| $C_{25}$ | $C_{26}$ | 1.3900 |
| $C_{27}$ | $C_{28}$ | 1.46(3) |
| $C_{27}$ | $C_{46}$ | 1.53(3) |
| $C_{27}$ | $N_2$ | 1.47(3) |
| $C_{28}$ | $O_2$ | 1.38(3) |
| $C_{29}$ | $C_{30}$ | 1.40(3) |
| $C_{29}$ | $N_2$ | 1.36(3) |
| $C_{29}$ | $O_2$ | 1.34(2) |
| $C_{30}$ | $C_{31}$ | 1.37(3) |
| $C_{30}$ | $C_{35}$ | 1.46(3) |
| $C_{31}$ | $C_{32}$ | 1.46(3) |
| $C_{32}$ | $C_{33}$ | 1.41(3) |
| $C_{33}$ | $C_{34}$ | 1.37(3) |
| $C_{33}$ | $C_{36}$ | 1.53(3) |
| $C_{34}$ | $C_{35}$ | 1.25(3) |
| $C_{36}$ | $N_4$ | 1.29(3) |
| $C_{36}$ | $O_4$ | 1.26(3) |
| $C_{37}$ | $C_{38}$ | 1.47(3) |
| $C_{37}$ | $O_4$ | 1.35(2) |
| $C_{38}$ | $C_{39}$ | 1.66(3) |
| $C_{38}$ | $N_4$ | 1.43(3) |
| $C_{39}$ | $C_{40}$ | 1.59(2) |
| $C_{40}$ | $C_{41}$ | 1.3900 |
| $C_{40}$ | $C_{45}$ | 1.3900 |
| $C_{41}$ | $C_{42}$ | 1.3900 |
| $C_{42}$ | $C_{43}$ | 1.3900 |
| $C_{43}$ | $C_{44}$ | 1.3900 |

| Atom | Atom | Length/Å |
|---|---|---|
| $C_{44}$ | $C_{45}$ | 1.3900 |
| $C_{46}$ | $C_{47}$ | 1.49(2) |
| $C_{47}$ | $C_{48}$ | 1.3900 |
| $C_{47}$ | $C_{52}$ | 1.3900 |
| $C_{48}$ | $C_{49}$ | 1.3900 |
| $C_{49}$ | $C_{50}$ | 1.3900 |
| $C_{50}$ | $C_{51}$ | 1.3900 |
| $C_{51}$ | $C_{52}$ | 1.3900 |
| $N_1$ | $Pt_1$ | 2.141(18) |
| $N_2$ | $Pt_1$ | 2.025(14) |
| $N_3$ | $Pt_2$ | 2.080(16) |
| $N_4$ | $Pt_2$ | 2.152(13) |
| $C_{53}$ | $C_{67}{}^1$ | 1.44(8) |
| $C_{53}$ | $N_5$ | 1.19(4) |
| $C_{53}$ | $O_5$ | 1.42(4) |
| $C_{54}$ | $C_{55}$ | 1.73(5) |
| $C_{54}$ | $O_5$ | 1.38(5) |
| $C_{55}$ | $C_{56}$ | 1.61(3) |
| $C_{55}$ | $N_5$ | 1.45(4) |
| $C_{56}$ | $C_{57}$ | 1.32(3) |
| $C_{57}$ | $C_{58}$ | 1.3900 |
| $C_{57}$ | $C_{62}$ | 1.3900 |
| $C_{58}$ | $C_{59}$ | 1.3900 |
| $C_{59}$ | $C_{60}$ | 1.3900 |
| $C_{60}$ | $C_{61}$ | 1.3900 |
| $C_{61}$ | $C_{62}$ | 1.3900 |
| $C_{63}$ | $C_{64}$ | 1.60(3) |
| $C_{63}$ | $N_6$ | 1.36(4) |
| $C_{63}$ | $O_6$ | 1.43(4) |
| $C_{64}$ | $C_{65}$ | 1.3900 |
| $C_{64}$ | $C_{69}$ | 1.3900 |
| $C_{65}$ | $C_{66}$ | 1.3900 |
| $C_{66}$ | $C_{67}$ | 1.3900 |
| $C_{67}$ | $C_{53}{}^1$ | 1.44(4) |
| $C_{67}$ | $C_{68}$ | 1.3900 |
| $C_{68}$ | $C_{69}$ | 1.3900 |
| $C_{70}$ | $C_{71}$ | 1.51(3) |
| $C_{70}$ | $O_6$ | 1.42(2) |
| $C_{71}$ | $C_{72}$ | 1.38(4) |
| $C_{71}$ | $N_6$ | 1.45(4) |
| $C_{72}$ | $C_{73}$ | 1.36(4) |
| $C_{73}$ | $C_{74}$ | 1.3900 |
| $C_{73}$ | $C_{78}$ | 1.3900 |
| $C_{74}$ | $C_{75}$ | 1.3900 |
| $C_{75}$ | $C_{76}$ | 1.3900 |
| $C_{76}$ | $C_{77}$ | 1.3900 |
| $C_{77}$ | $C_{78}$ | 1.3900 |
| $N_5$ | $Pt_3$ | 1.99(3) |
| $N_6$ | $Pt_3$ | 2.09(2) |
| $N_7$ | $O_7$ | 1.09(3) |
| $N_7$ | $O_8$ | 1.24(3) |
| $N_7$ | $O_9$ | 1.29(3) |

[1]-X, +Y, -Z

Typical bond angle data for crystal are listed as follows:

| Atom | Atom | Atom | Angle/° | Atom | Atom | Atom | Angle/° |
|---|---|---|---|---|---|---|---|
| $N_1$ | $C_1$ | $C_4$ | 126.5(18) | $C_{52}$ | $C_{47}$ | $C_{46}$ | 118.1(12) |
| $O_1$ | $C_1$ | $C_4$ | 121.9(17) | $C_{47}$ | $C_{48}$ | $C_{49}$ | 120.0 |
| $O_1$ | $C_1$ | $N_1$ | 111.6(17) | $C_{50}$ | $C_{49}$ | $C_{48}$ | 120.0 |
| $O_1$ | $C_2$ | $C_3$ | 104.6(17) | $C_{49}$ | $C_{50}$ | $C_{51}$ | 120.0 |
| $C_{20}$ | $C_3$ | $C_2$ | 108.5(19) | $C_{52}$ | $C_{51}$ | $C_{50}$ | 120.0 |
| $N_1$ | $C_3$ | $C_2$ | 100.0(17) | $C_{51}$ | $C_{52}$ | $C_{47}$ | 120.0 |
| $N_1$ | $C_3$ | $C_{20}$ | 106.5(14) | $C_1$ | $N_1$ | $C_3$ | 108.4(16) |
| $C_1$ | $C_4$ | $C_5$ | 116.8(17) | $C_1$ | $N_1$ | $Pt_1$ | 126.7(13) |
| $C_9$ | $C_4$ | $C_1$ | 120.8(19) | $C_3$ | $N_1$ | $Pt_1$ | 124.9(13) |
| $C_9$ | $C_4$ | $C_5$ | 122.2(19) | $C_{27}$ | $N_2$ | $Pt_1$ | 128.5(13) |
| $C_6$ | $C_5$ | $C_4$ | 121.1(19) | $C_{29}$ | $N_2$ | $C_{27}$ | 102.2(16) |
| $C_5$ | $C_6$ | $C_7$ | 118(2) | $C_{29}$ | $N_2$ | $Pt_1$ | 128.8(13) |
| $C_8$ | $C_7$ | $C_6$ | 119.8(18) | $N_3$ | $C_{12}$ | $C_{12}$ | 109.5(15) |
| $C_8$ | $C_7$ | $C_{10}$ | 122.6(17) | $C_{10}$ | $N_3$ | $Pt_2$ | 126.9(11) |
| $C_{10}$ | $C_7$ | $C_6$ | 117.6(16) | $C_{12}$ | $N_3$ | $Pt_2$ | 123.1(11) |
| $C_7$ | $C_8$ | $C_9$ | 124.3(19) | $C_{36}$ | $N_4$ | $C_{38}$ | 102.6(16) |
| $C_4$ | $C_9$ | $C_8$ | 114.0(19) | $C_{36}$ | $N_4$ | $Pt_2$ | 130.1(14) |

| Atom | Atom | Atom | Angle/° | Atom | Atom | Atom | Angle/° |
|---|---|---|---|---|---|---|---|
| $N_3$ | $C_{10}$ | $C_7$ | 127.9(15) | $C_{38}$ | $N_4$ | $Pt_2$ | 127.3(12) |
| $N_3$ | $C_{10}$ | $O_3$ | 119.3(16) | $C_1$ | $O_1$ | $C_2$ | |
| $O_3$ | $C_{10}$ | $C_7$ | 112.8(17) | $C_{29}$ | $O_2$ | $C_{28}$ | |
| $O_3$ | $C_{11}$ | $C_{12}$ | 101.6(12) | $C_{10}$ | $O_3$ | $C_{11}$ | |
| $C_{13}$ | $C_{12}$ | $C_{11}$ | 115.5(15) | $C_{36}$ | $O_4$ | $C_{37}$ | |
| $C_{13}$ | $C_{12}$ | $N_3$ | 115.1(14) | $N_2$ | $Pt_1$ | $N_1$ | |
| $N_3$ | $C_{12}$ | $C_{11}$ | 102.6(14) | $N_3$ | $Pt_2$ | $N_4$ | |
| $C_{12}$ | $C_{13}$ | $C_{14}$ | 115.2(16) | $N_5$ | $C_{53}$ | $C_{67}{}^1$ | |
| $C_{15}$ | $C_{14}$ | $C_{13}$ | 118.9(12) | $N_5$ | $C_{53}$ | $O_5$ | |
| $C_{15}$ | $C_{14}$ | $C_{19}$ | 120.0 | $O_5$ | $C_{53}$ | $C_{67}{}^1$ | |
| $C_{19}$ | $C_{14}$ | $C_{13}$ | 121.0(12) | $O_5$ | $C_{54}$ | $C_{55}$ | |
| $C_{14}$ | $C_{15}$ | $C_{16}$ | 120.0 | $C_{56}$ | $C_{55}$ | $C_{54}$ | |
| $C_{17}$ | $C_{16}$ | $C_{15}$ | 120.0 | $N_5$ | $C_{55}$ | $C_{54}$ | |
| $C_{16}$ | $C_{17}$ | $C_{18}$ | 120.0 | $N_5$ | $C_{55}$ | $C_{56}$ | |
| $C_{19}$ | $C_{18}$ | $C_{17}$ | 120.0 | $C_{57}$ | $C_{56}$ | $C_{55}$ | |
| $C_{18}$ | $C_{19}$ | $C_{14}$ | 120.0 | $C_{56}$ | $C_{57}$ | $C_{58}$ | |
| $C_{21}$ | $C_{20}$ | $C_3$ | 109.8(17) | $C_{56}$ | $C_{57}$ | $C_{62}$ | |
| $C_{22}$ | $C_{21}$ | $C_{20}$ | 119.8(13) | $C_{58}$ | $C_{57}$ | $C_{62}$ | |
| $C_{22}$ | $C_{21}$ | $C_{26}$ | 120.0 | $C_{57}$ | $C_{58}$ | $C_{59}$ | |
| $C_{26}$ | $C_{21}$ | $C_{20}$ | 120.2(13) | $C_{60}$ | $C_{59}$ | $C_{58}$ | |
| $C_{21}$ | $C_{22}$ | $C_{23}$ | 120.0 | $C_{61}$ | $C_{60}$ | $C_{59}$ | |
| $C_{22}$ | $C_{23}$ | $C_{24}$ | 120.0 | $C_{60}$ | $C_{61}$ | $C_{62}$ | |
| $C_{25}$ | $C_{24}$ | $C_{23}$ | 120.0 | $C_{61}$ | $C_{62}$ | $C_{57}$ | 120.0 |
| $C_{24}$ | $C_{25}$ | $C_{26}$ | 120.0 | $N_6$ | $C_{63}$ | $C_{64}$ | 130(2) |
| $C_{25}$ | $C_{26}$ | $C_{21}$ | 120.0 | $N_6$ | $C_{63}$ | $O_6$ | 124(2) |
| $C_{28}$ | $C_{27}$ | $C_{46}$ | 117.3(19) | $O_6$ | $C_{63}$ | $C_{64}$ | 104(2) |
| $C_{28}$ | $C_{27}$ | $N_2$ | 106.9(18) | $C_{65}$ | $C_{64}$ | $C_{63}$ | 115.8(18) |
| $N_2$ | $C_{27}$ | $C_{46}$ | 107.7(17) | $C_{65}$ | $C_{64}$ | $C_{69}$ | 120.0 |
| $O_2$ | $C_{28}$ | $C_{27}$ | 107.6(18) | $C_{69}$ | $C_{64}$ | $C_{63}$ | 123.4(18) |
| $N_2$ | $C_{29}$ | $C_{30}$ | 120.9(18) | $C_{66}$ | $C_{65}$ | $C_{64}$ | 120.0 |
| $O_2$ | $C_{29}$ | $C_{30}$ | 121.3(19) | $C_{65}$ | $C_{66}$ | $C_{67}$ | 120.0 |
| $O_2$ | $C_{29}$ | $N_2$ | 116.9(18) | $C_{66}$ | $C_{67}$ | $C_{53}{}^1$ | 119(2) |
| $C_{29}$ | $C_{30}$ | $C_{35}$ | 121.5(19) | $C_{68}$ | $C_{67}$ | $C_{53}{}^1$ | 120(2) |
| $C_{31}$ | $C_{30}$ | $C_{29}$ | 116.9(19) | $C_{68}$ | $C_{67}$ | $C_{66}$ | 120.0 |
| $C_{31}$ | $C_{30}$ | $C_{35}$ | 118.9(19) | $C_{69}$ | $C_{68}$ | $C_{67}$ | 120.0 |
| $C_{30}$ | $C_{31}$ | $C_{32}$ | 117.5(18) | $C_{68}$ | $C_{69}$ | $C_{64}$ | 120.0 |
| $C_{33}$ | $C_{32}$ | $C_{31}$ | 119.1(18) | $O_6$ | $C_{70}$ | $C_{71}$ | 112(3) |
| $C_{32}$ | $C_{33}$ | $C_{36}$ | 114.4(18) | $C_{72}$ | $C_{71}$ | $C_{70}$ | 118(3) |
| $C_{34}$ | $C_{33}$ | $C_{32}$ | 117.5(18) | $C_{72}$ | $C_{71}$ | $N_6$ | 114(3) |
| $C_{34}$ | $C_{33}$ | $C_{36}$ | 127.9(19) | $N_6$ | $C_{71}$ | $C_{70}$ | 106(3) |
| $C_{35}$ | $C_{34}$ | $C_{33}$ | 126.2(19) | $C_{73}$ | $C_{72}$ | $C_{71}$ | 131(3) |
| $C_{34}$ | $C_{35}$ | $C_{30}$ | 119.3(19) | $C_{72}$ | $C_{73}$ | $C_{74}$ | 118.3(19) |
| $N_4$ | $C_{36}$ | $C_{33}$ | 121(2) | $C_{72}$ | $C_{73}$ | $C_{78}$ | 121.0(19) |
| $O_4$ | $C_{36}$ | $C_{33}$ | 119(2) | $C_{74}$ | $C_{73}$ | $C_{78}$ | 120.0 |
| $O_4$ | $C_{36}$ | $N_4$ | 120(2) | $C_{75}$ | $C_{74}$ | $C_{73}$ | 120.0 |
| $O_4$ | $C_{37}$ | $C_{38}$ | 105.4(16) | $C_{74}$ | $C_{75}$ | $C_{76}$ | 120.0 |
| $C_{37}$ | $C_{38}$ | $C_{39}$ | 108.9(19) | $C_{77}$ | $C_{76}$ | $C_{75}$ | 120.0 |
| $N_4$ | $C_{38}$ | $C_{37}$ | 104.9(18) | $C_{76}$ | $C_{77}$ | $C_{78}$ | 120.0 |
| $N_4$ | $C_{38}$ | $C_{39}$ | 104.6(17) | $C_{77}$ | $C_{78}$ | $C_{73}$ | 120.0 |
| $C_{40}$ | $C_{39}$ | $C_{38}$ | 114.9(16) | $C_{53}$ | $N_5$ | $C_{55}$ | 107(3) |
| $C_{41}$ | $C_{40}$ | $C_{39}$ | 120.8(12) | $C_{53}$ | $N_5$ | $Pt_3$ | 129(2) |
| $C_{41}$ | $C_{40}$ | $C_{45}$ | 120.0 | $C_{55}$ | $N_5$ | $Pt_3$ | 124(2) |
| $C_{45}$ | $C_{40}$ | $C_{39}$ | 119.2(12) | $C_{63}$ | $N_6$ | $C_{71}$ | 100(2) |
| $C_{40}$ | $C_{41}$ | $C_{42}$ | 120.0 | $C_{63}$ | $N_6$ | $Pt_3$ | 130.3(17) |
| $C_{41}$ | $C_{42}$ | $C_{43}$ | 120.0 | $C_{71}$ | $N_6$ | $Pt_3$ | 128(2) |
| $C_{42}$ | $C_{43}$ | $C_{44}$ | 120.0 | $C_{54}$ | $O_5$ | $C_{53}$ | 101(3) |
| $C_{45}$ | $C_{44}$ | $C_{43}$ | 120.0 | $C_{70}$ | $O_6$ | $C_{63}$ | 96(2) |
| $C_{44}$ | $C_{45}$ | $C_{40}$ | 120.0 | $N_5$ | $Pt_3$ | $N_6$ | 176.0(11) |
| $C_{47}$ | $C_{46}$ | $C_{27}$ | 117.0(17) | $O_7$ | $N_7$ | $O_8$ | 126(3) |
| $C_{48}$ | $C_{47}$ | $C_{46}$ | 121.6(12) | $O_7$ | $N_7$ | $O_9$ | 123(2) |
| $C_{48}$ | $C_{47}$ | $C_{52}$ | 120.0 | $O_8$ | $N_7$ | $O_9$ | 104(3) |

[1]-X, +Y, -Z

Condensation Reaction Between Benzophenone Imine and Trimethylsilitrile

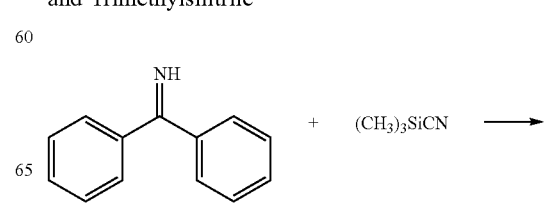

-continued

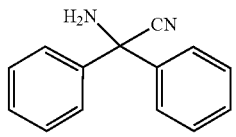

0.025 mL of benzophenone imine and 0.4 mL of trimethylsilitrile was taken and added to a 25 mL small flask, then, 1 mL of THF and 0.0157 g of the compound I were added, and stirred at room temperature for 8 hrs. A small number of the sample was taken for nuclear magnetic detection. The conversion rate was more than 99%; $^1$H NMR (600 MHz, CDCl$_3$, 27° C.), δ7.23-7.59 (m, 10H), 4.10 (s, 2H).

Application of Anti-Cancer Activity

Platinum complex designed and synthesized according to the structure of the active natural product in the present application exhibits strong inhibitory activity ($ED_{50}$<10.0 μg/mL) for the treatment of A549 (lung cancer), KB (nasopharyngeal carcinoma), KB-VIn (anti-drug-resistant nasopharyngeal carcinoma) and human breast cancer (MCF-7). Therefore, it is expected that this compound can be used to treat various kinds of cancers, including lung cancer, breast cancer, oral cancer cells, and breast cancer cells. Part of this compound's anti-cancer activity test results are listed in Table 1:

TABLE 1

Anti-cancer Activity Data of Platinum Complex (I)

| | Cell line | | | | | | | |
|---|---|---|---|---|---|---|---|---|
| | Human lung cancer cells A549 | | Human breast cancer cell MDA-MB-231 | | Human oral cancer cells KB-VIN | | Human breast cancer cell MCF-7 | |
| Sample | Average value | Standard deviation | Average value | Standard deviation | Average value | Standard deviation | Average value | Standard deviation |
| Platinum complex (I) | 6.12 | ±0.22 | 6.92 | ±0.13 | 4.06 | ±0.13 | 2.43 | ±0.02 |
| Cisplatin | 4.96 | ±0.09 | 26.41 | ±0.74 | 3.01 | ±0.07 | 29.99 | ±0.93 |

What is claimed is:

1. A method for condensation of benzophenone imine and trimethylsilitrile comprising using the chiral platinum complex having a chemical formula (I):

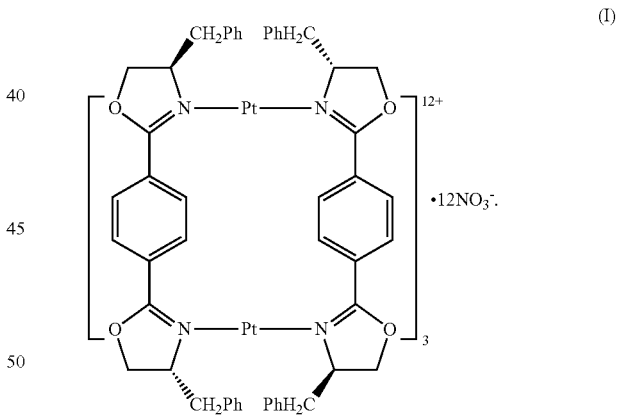

* * * * *